United States Patent [19]

Roeper et al.

[11] Patent Number: 4,962,243

[45] Date of Patent: Oct. 9, 1990

[54] PREPARATION OF OCTADIENOLS

[75] Inventors: Michael Roeper, Wachenheim; Werner Bertleff, Viernheim; Dieter Koeffer, Ludwigshafen, all of Fed. Rep. of Germany

[73] Assignee: BASF Aktiengesellschaft, Ludwigshafen, Fed. Rep. of Germany

[21] Appl. No.: 315,312

[22] Filed: Feb. 24, 1989

[30] Foreign Application Priority Data

Feb. 27, 1988 [DE] Fed. Rep. of Germany ....... 3806305

[51] Int. Cl.$^5$ ...................... C07C 29/00; C07C 33/02
[52] U.S. Cl. ................................................ 568/909.5
[58] Field of Search ...................... 568/898, 900, 909.5

[56] References Cited

U.S. PATENT DOCUMENTS 3,534,088 10/1970 Bryant et al. ...................... 568/841
3,670,029 6/1972 Romanelli et al. ............. 260/612 D

FOREIGN PATENT DOCUMENTS

| 287066 | 10/1988 | European Pat. Off. . |
| 2011163 | 10/1970 | Fed. Rep. of Germany . |
| 2018054 | 11/1970 | Fed. Rep. of Germany . |
| 303652 | 12/1982 | U.S.S.R. . |
| 2074156 | 10/1981 | United Kingdom . |

OTHER PUBLICATIONS

Patents Abstracts of Japan, (Kokai No. 53-147013).
F. A. Cotton, et al., Anorganische Chemie, 3rd edition, Verlag Chemie, Interscience Publishers, pp. 179, 238, 394 and 506.
Chem. Abstracts 80, Oct. 20, 1973, 59446C, (Japan, Kokai 73/78,107).

*Primary Examiner*—J. E. Evans
*Attorney, Agent, or Firm*—Oblon, Spivak, McClelland, Maier & Neustadt

[57] ABSTRACT

Octadienols are prepared by teleomerization of 1,3-butadiene with water in the presence of carbon dioxide and a catalyst system comprising a palladium compound and a tertiary phosphorus compound by performing the reaction in the presence of a strong non-coordinating acid.

19 Claims, No Drawings

PREPARATION OF OCTADIENOLS

The present invention relates to an improved process for preparing octadienols by telomerization of buta-1,3-diene (butadiene) with water in the presence of carbon dioxide and a catalyst system comprising a palladium compound and a tertiary phosphorus compound.

Octadienols are usable inter alia as intermediates for preparing octyl alcohols which in turn are useful for preparing plasticizers such as dioctyl phthalate. Since, of the octyl alcohols, preference is given to 1-octanol, the most important octadienols are those which, like octa-2,7-dien-1-ol, are convertible into 1-octanol, but it is precisely these octadienols which have hitherto only been available in inadequate yields.

DE-A-2,018,054 discloses that the telomerization of butadiene with water in the presence of carbon dioxide, a solvent and a catalyst system comprising a palladium(0) or -(II) compound and a tertiary phosphine or phosphite gives octadienols

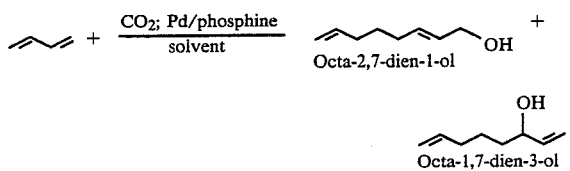
Octa-2,7-dien-1-ol

Octa-1,7-dien-3-ol together with octadienyl ether and polyenes such as 1,3,7-octatriene as byproducts.

However, both the octadienol yields and the selectivity in respect of octa-2,7-dien-1-ol are still unsatisfactory.

Furthermore, the telomerization of butadiene with water in the presence of palladium(II) diacetate and triphenylphosphine as a catalyst system together with formic acid and dioxane gives octadienols (CA 80 (1973), 59446e JP-B-73/78,107). The disadvantges with this reaction are the low overall yield of 62% of octadienols and the long reaction time of 17 hours.

It is an object of the present invention to eliminate the disadvantages mentioned and, more particularly, to make octa-2,7-dien-1-ol available in higher yields than hitherto.

We have found that this object is achieved with a process for preparing an octadienol by telomerizing 1,3-butadiene with water in the presence of carbon dioxide and a catalyst system comprising a palladium compound and a tertiary phosphorus compound, which is carried out in the presence of a strong noncoordinating acid.

A noncoordinating acid is an acid whose anions do not form stable complexes with transition metal cations such as palladium. Details concerning the theory of non-coordinating acids may be found in the textbook by F. A. Cotton and G. Wilkinson, Anorganische Chemie, 3rd edition, VerLag Chemie, Interscience Publishers, pages 179, 238, 394 and 506.

Strong noncoordinating acids suitable for the purposes according to the invention are accordingly in particular tetrafluoroboric acid, hexafluorophosphoric acid, methanesulfonic acid, trifluoromethanesulfonic acid, sulfuric acid, trifluoroacetic acid, trichloroacetic acid and p-toluenesulfonic acid. Fatty acids are likewise non-coordinating, so that it is also possible to use for example acetic acid, which for the present purposes is still regarded as a strong acid. However, weaker acids than acetic acid will in general not be used, since the effect which the acid is to bring about according to the invention generally decreases with decreasing acid strength.

Coordinating and hence unsuitable acids are first and foremost halohydric acids such as HCl, since the anions thereof form stable complexes with palladium of the type $[PdCl_4]^{2-}$, $[Pd_2Cl_6]^{2-}$ or $[PdCl_3L]^-$, where L is a ligand of a tertiary phosphine or phosphite; and stable complexes of this type no longer have any catalytic activity of the kind required for the telomerization of butadiene. Which acids are suitable in a particular case, and which are not, is easy to determine by reference to the present teaching, if necessary by means of a few preliminary trials.

Although the mechanism behind the action of the acid is not as yet known, it is likely that the proton of the acid combines with the $\pi$-allyl system of the butadiene-palladium complex to form a cation with which a hydroxyl group forms an adduct more readily than with the electrically neutral system.

The ratio of acid : palladium is in general from 0.1 to 150, preferably from 50 to 100, equivalent % per mole of palladium.

Suitable for preparing the catalyst system are in principle all soluble palladium 0) and palladium(II) compounds except stable complexes of the abovementioned type and those compounds, for example palladium halides, which can convert into such stable complexes. Suitable palladium compounds are for example $Pd(OAc)_2$, $Pd(PPh_3)_4$, $Pd(dba)_2$ (dba=dibenzylidenacetone), $[Pd(acac)(PPh_3)_2]BF_4$ (acac=acetylacetone), $[Pd(h^3-C_3H_5)(COD)]BF_4$ (COD=1,5-cyclooctadiene) and $[Pd(acac)(COD)]BF_4$ and first and foremost palladium(II) acetylacetonate.

The amount of Pd compound is not critical, but is preferably from $10^{-5}$ to 0.1, in particular from $10^{-4}$ to $10^{-2}$, mole of palladium per mole of butadiene. The tertiary phosphorus compound acts as a stabilizing ligand L in the active palladium complexes of the type

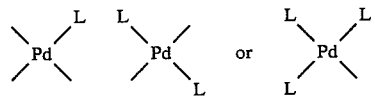

Suitable ligands L are basically all phosphines and phosphites, for example trialkylphosphines, triarylphosphines, and trialkyl and triaryl phosphites, having approximately up to 24 carbon atoms in total in the carbon radicals. Particular preference is given to triphenylphosphine, not least for economic reasons. In general, phosphines are preferable to phosphites, because the latter may hydrolyze with water and undergo rearrangements.

The amount of this ligand is in general from 1 to 20, preferably from 1 to 5, moles per mole of palladium.

The amount of carbon dioxide which promotes the telomerization of butadiene in a hitherto unrecognized manner is likewise not critical and may range from about $10^{-3}$ to 1, preferably from $10^{-2}$ to 0.5, mole per mole of butadiene.

Complete conversion of the butadiene to octadienol requires at least equimolar amounts of water (i.e. molar ratio of water:butadiene=0.5:1), but it is advisable to use a higher molar ratio of water:butadiene of up to about 10:1, preferably 5:1, in order to suppress the competing reactions leading to octadienyl ethers, octatriene and higher polyenes.

Suitable aprotic polar solvents are in particular ethers since they are inert under the reaction conditions and show sufficient to good solvency not only for butadiene but also for water. Specific examples are diethyl ether, tetrahydrofuran and 1,4-dioxane.

From a technical point of view it is particularly advisable to use those solvents which have a higher boiling point than the octadienols formed, since in such a case the octadienols can be isolated from the catalyst-containing solvent simply by distillation. Suitable high-boiling solvents are in particular polyalkylene glycol ethers of the formula

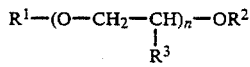

where $R^1$ and $R^2$ are each $C_1$–$C_3$-alkyl, $R^3$ is hydrogen or methyl and n is from 2 to 6, preferably 4.

Further suitable high-boiling solvents are dialkyl sulfoxides such as, in particular, dimethyl sulfoxide and sulfones such as tetrahydrothiophene 1,1-dioxide (sulfolane).

With the aid of high-boiling solvents, the process according to the invention may be carried out in a particularly advantageous continuous form by making the components mentioned react with one another in a reaction vessel R, transferring the reaction mixture from R into a distillation apparatus D, where unconverted butadiene and the octadienols are separated off as distillates from the fractional distillation, and recycling the butadiene and a catalyst-containing bottom product from D into R.

The reaction is preferably carried out at from 50° to 70° C. Below 50° C., particularly below 30° C., the reaction is too slow, and above 90° C., in particular above 100° C., there is the likelihood of undesirable secondary reactions which may become acceptable if great importance is placed on high space-time yields.

As regards the pressure, we recommend the autogenous pressure at the chosen reaction temperatures; it is usually within the range from 5 to 50, particularly from 10 to 30, bar.

An economically very advantageous form of the process according to the invention comprises using $C_4$ cuts instead of pure butadiene. $C_4$ cut olefins other than butadiene, namely 1-butene, 2-butene and isobutene, neither participate in nor impair the reaction. $C_4$ cuts contain about 45% by weight of butadiene, 17% by weight of 1-butene, 10% by weight of 2-butene and 25% by weight of isobutene, the remainder being butane and isobutane.

Otherwise the process according to the invention has no special technical features, so that no further elucidation is required.

The same is true of the working up of the reaction mixture.

The process according to the invention is notable for the fact that the high butadiene conversions of from about 80 to 100% are combined with particularly high selectivities in respect of octa-2,7-dien-1-ol of the order of from about 75 to 90%, values not obtainable with prior art methods.

EXAMPLE 1

In a 300 ml of autoclave, a mixture of 127 ml of a solvent, 30 g (1.67 mol) of water, 0.22 g (0.72 mmol) of palladium(II) acetylacetonate, 0.56 g (2.16 mmol) of triphenylphosphine and 0.032 g (0.36 mmol) of tetrafluoroboric acid were pressurized with 22.5 g (416 mmol) of butadiene and 4.4 g (100 mmol) of carbon dioxide under argon as a protective gas, and afterwards the mixture was stirred at 50° C. for 8 hours.

Thereafter the clear slightly yellow single-phase liquid reactor output was analyzed by capillary gas chromatography (internal standard n-decanol).

The same runs were repeated without the acid $HBF_4$ (comparative runs 1a and 2a). Further details concerning these runs and the results thereof may be found in Table 1.

TABLE 1

| Run No. | Solvent | Conversion [%] | Selectivity [mol %] | | |
|---|---|---|---|---|---|
| | | | $C_8$-2,7-dien-1-ol | $C_8$-1,7-dien-3-ol | $C_8$ and $C_{12}$-polyenes |
| 1 | Dimethyl sulfoxide | 88 | 86.5 | 3.9 | 4.4 |
| 1a* | Dimethyl sulfoxide | 83 | 74.7 | 4.0 | 15.9 |
| 2 | Tetraethylene glycol dimethyl ether | 95 | 79.5 | 7.9 | 8.1 |
| 2a* | Tetraethylene glycol dimethyl ether | 62 | 81.4 | 7.9 | 7.6 |

*without $HBF_4$

EXAMPLE 2

Run 2 of Example 1 was repeated at 60° C. using 0.7 g (16 mmol) of carbon dioxide to prepare a reaction mixture which was subsequently subjected to a thin-film distillation at 100° C. and 4 mbar to separate the products.

The catalyst-containing bottom product was then admixed with those amounts of fresh starting materials removed in the course of distillation, the mixtures used for a further run of the same type. This cycle was repeated five times in total. From the results summarized in Table 2 it can be seen that catalyst activity remained virtually constant with repeated use of the bottom phase.

TABLE 2

| Run No. | Conversion [%] | Selectivity [mol %] | | |
|---|---|---|---|---|
| | | $C_8$-2,7-dien-1-ol | $C_8$-1,7-dien-3-ol | $C_8 + C_{12}$-polyenes |
| 1 | 88 | 77.2 | 8.7 | 10.4 |
| 2 | 90 | 81.7 | 5.9 | 7.1 |
| 3 | 82 | 77.8 | 6.0 | 8.9 |
| 4 | 92 | 81.6 | 4.9 | 7.6 |
| 5 | 85 | 85.4 | 5.5 | 8.1 |
| 6 | 88 | 86.1 | 6.6 | 4.8 |

EXAMPLE 3

Run 2 of Example 1 was repeated with 15 g (0.83 mol) of water to test various noncoordinating acids in an equivalence ratio of acid: palladium of 0.5:1 in respect of a catalytic effect.

The details of these runs and the results thereof may be found in Table 3.

TABLE 3

| Run No. | Acid | Conversion [mol %] | Selectivity [mol %] | | |
|---|---|---|---|---|---|
| | | | $C_8$-2,7-dien-1-ol | $C_8$-1,7-dien-3-ol | $C + C_{12}$-polyenes |
| 1 | $HBF_4$ | 100 | 79.5 | 10.3 | 6.1 |
| 2 | $HPF_6$ | 81 | 80.5 | 6.5 | 6.9 |
| 3 | p-$CH_3$-Ph-$SO_3H$(b) | 72 | 75.7 | 12.0 | 7.8 |
| 4 | $H_2SO_4$ | 91 | 69.4 | 15.4 | 9.4 |
| 5 | $CF_3CO_2H$ | 77 | 59.9 | 23.1 | 7.9 |
| 6a(*) | — | 73 | 63.4 | 22.5 | 11.9 |

(*) for comparison without acid
(b) p-toluenesulfonic acid

EXAMPLE 4

The effect of the equivalence ratio of acid:palladium can be seen from the runs of Table 4 which were carried out similarly to run 2 of Example 1, except that 15 g (0.83 mol) of water were used.

TABLE 4

| Run No. | $HBF_4$/Pd | Conversion [mol %] | Selectivity [mol %] | | |
|---|---|---|---|---|---|
| | | | $C_8$-2,7-dien-1-ol | $C_8$-2,7-dien-3-ol | $C + C_{12}$ polyenes |
| 1(*) | 0 | 73 | 63.4 | 22.5 | 11.9 |
| 2 | 25 | 74 | 72.4 | 17.3 | 8.7 |
| 3 | 50 | 100 | 79.5 | 10.3 | 6.1 |
| 4 | 75 | 84 | 82.3 | 6.8 | 4.4 |
| 5 | 100 | 70 | 80.2 | 5.7 | 8.0 |

(*)without addition of acid

EXAMPLE 5

The quantities used and the processing corresponded to the experimental conditions of Example 1, run 2, except that 15 g (0.83 mol) of water were used.

The butadiene, however, was used in the form of a $C_4$ cut prepared by mixing in raffinate I consisting of 29% of 1-butene, 16% of 2-butene, 45% of isobutene and 10% of butanes. For comparison, a reaction was carried out with pure butadiene (run 2), which shows that the presence of the other alkenes in the $C_4$ cut does not impair the telomerization of the butadiene.

TABLE 5

| Run No. | Temp. [°C.] | Butadiene in $C_4$ cut [%] | Conversion [%] | Selectivity [mol %] | | |
|---|---|---|---|---|---|---|
| | | | | $C_8$-2,7-dien-1-ol | $C_8$-1,7-dien-3-ol | $C_8 + C_{12}$-polyenes |
| | | Feed Bleed | | | | |
| 1 | 50 | 38   2.5 | 94 | 78.2 | 4.3 | 7.0 |
| 2* | 50 | 100   — | 99 | 78.0 | 7.9 | 8.3 |
| 3 | 60 | 45   7.6 | 86 | 81.1 | 6.5 | 6.5 |
| 4 | 70 | 45   2.3 | 90 | 77.0 | 4.9 | 10.1 |

*Feed of pure butadiene (comparison)

We claim:

1. A process for preparing an octadienol, comprising: telomerizing 1,3-butadiene with water in the presence of carbon dioxide, a non-coordinating acid and a catalyst system comprised of a palladium compound and a tertiary phosphorus compound, the ratio of acid to palladium in said palladium compound ranging from 0.1:150 equivalent % per mole of palladium and the amount of palladium compound employed relative to butadiene reactant ranging from $10^{-5}$ to 0.1 mole of palladium per mole of butadiene.

2. The process of claim 1, wherein said non-coordinating acid is a member selected from the group consisting of tetrafluoroboric acid, hexafluorophosphoric acid, methanesulfonic acid, trifluoromethane sulfonic acid, p-toluenesulfonic acid, sulfuric acid, trifluoroacetic acid, trichloroacetic acid and acetic acid.

3. The process of claim 1, wherein said ratio ranges from 50:100.

4. The process of claim 1, wherein the palladium compound is a palladium (0) or palladium (II) compound.

5. The process of claim 4, wherein said palladium compound is Pd(acac)$_2$, Pd(OAc)$_2$, Pd(PPh$_3$)$_4$, Pd(dba)$_2$, [Pd(acac)(PPh$_3$)$_2$]BF$_4$, [Pd(h$^3$-C$_3$H$_5$)(COD)]BF$_4$, or [Pd(acac)(COD)]BF$_4$.

6. The process of claim 1, wherein said amount of palladium compound ranges from $10^{-4}$ to $10^{-2}$ mole of palladium per mole of butadiene.

7. The process of claim 1, wherein said tertiary phosphorus compound is a trialkylphosphine, a triarylphosphine, a trialkylphosphite or a triarylphosphite.

8. The process of claim 1, wherein the amount of tertiary phosphorus compound as a ligand ranges from 1 to 20 moles per mole of said palladium compound.

9. The process of claim 8, wherein said amount of phosphorus ligand ranges from 1–5 moles per mole of palladium.

10. The process of claim 1, wherein the amount of carbon dioxide present ranges from $10^{-3}$ to 1 mole per mole of butadiene.

11. The process of claim 10, wherein said amount of carbon dioxide ranges from $10^{-2}$ to 0.5 mole of carbon dioxide.

12. The process of claim 1, wherein the amount of water in the reaction system is at least an equimolar amount with respect to butadiene reactant.

13. The process of claim 1, wherein the reaction medium further contains an aprotic polar solvent in which water and 1,3-butadiene are partially soluble.

14. The process of claim 13, wherein the aprotic solvent has a boiling point higher than the octadienol product prepared.

15. The process of claim 14, wherein said solvent is a polyalkylene glycol ether.

16. The process of claim 14, wherein said solvent is a sulfoxide or sulfone.

17. The process of claim 1, wherein said 1,3-butadiene reactant is a mixture of said 1,3-butadiene with another saturated or olefinic $C_4$ hydrocarbon.

18. The process of claim 1, wherein said reaction is conducted at a temperature ranging from 50°–70° C.

19. The process of claim 1, wherein the telomerization reaction is conducted under a pressure ranging from 5–50 bar.

* * * * *